US008604396B2

(12) United States Patent
Takenouchi

(10) Patent No.: US 8,604,396 B2
(45) Date of Patent: Dec. 10, 2013

(54) CERAMIC HEATER, OXYGEN SENSOR AND HAIR IRON THAT USE THE CERAMIC HEATER

(75) Inventor: Hiroshi Takenouchi, Kirishima (JP)

(73) Assignee: Kyocera Corporation, Kyoto (JP)

( * ) Notice: Subject to any disclaimer, the term of this patent is extended or adjusted under 35 U.S.C. 154(b) by 522 days.

(21) Appl. No.: 12/739,941

(22) PCT Filed: Oct. 28, 2008

(86) PCT No.: PCT/JP2008/069557
§ 371 (c)(1),
(2), (4) Date: Jul. 19, 2010

(87) PCT Pub. No.: WO2009/057595
PCT Pub. Date: May 7, 2009

(65) Prior Publication Data
US 2010/0294300 A1 Nov. 25, 2010

(30) Foreign Application Priority Data
Oct. 29, 2007 (JP) ................. 2007-280307

(51) Int. Cl.
H05B 3/48 (2006.01)
A45D 1/04 (2006.01)
(52) U.S. Cl.
USPC ............................ 219/544; 132/229; 219/541
(58) Field of Classification Search
USPC ........................... 219/541, 542, 544; 132/229
See application file for complete search history.

(56) References Cited

U.S. PATENT DOCUMENTS

| 7,078,659 | B2 | 7/2006 | Yokoyama et al. | 219/544 |
|---|---|---|---|---|
| 2005/0236398 | A1* | 10/2005 | Yokoyama et al. | 219/544 |
| 2007/0043399 | A1* | 2/2007 | Stevenson et al. | 607/37 |
| 2007/0221661 | A1 | 9/2007 | Nagasako et al. | 219/544 |

FOREIGN PATENT DOCUMENTS

| JP | 2003100421 A | * | 4/2003 |
|---|---|---|---|
| JP | 2005-190740 | | 7/2005 |
| JP | 2005-331502 | | 12/2005 |
| JP | 2007-022908 | | 2/2007 |

OTHER PUBLICATIONS

English language machine translation of JP2003100421A.*

* cited by examiner

Primary Examiner — Matthew W Such
Assistant Examiner — Robert Carpenter
(74) Attorney, Agent, or Firm — DLA Piper LLP (US)

(57) ABSTRACT

To provide a ceramic heater that has high durability by increasing the bonding strength between the lead member and the brazing material, the ceramic heater comprises a ceramic base, a heating resistor embedded in the ceramic base, an external electrode that is disposed on side face of the ceramic base and is electrically connected to the heating resistor, and a lead member brazed onto the external electrodes, wherein the distance between a point in the brazed portion of the periphery of the lead member and a center of the lead member is smaller than the distance between an another point in the brazed portion and the center, in a section of the lead member perpendicular to the longitudinal direction of the lead member.

6 Claims, 7 Drawing Sheets

Fig. 1
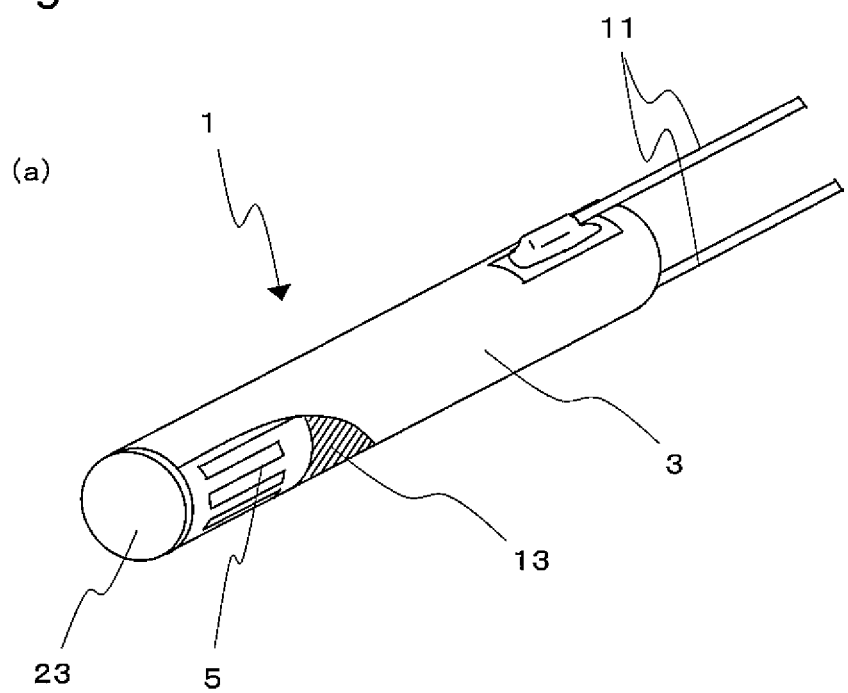
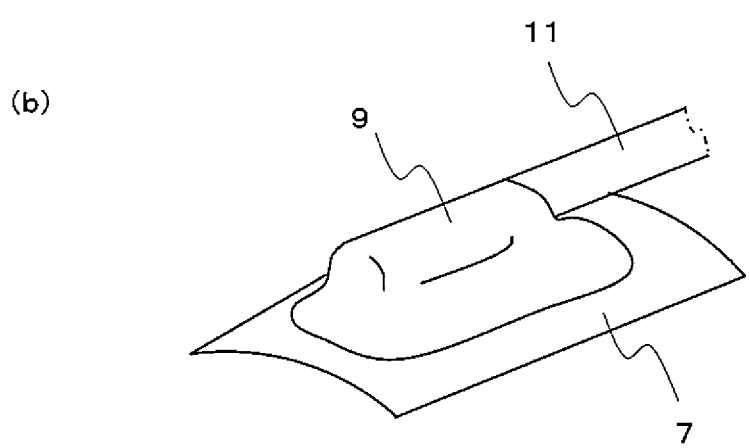

Fig. 2
(a)
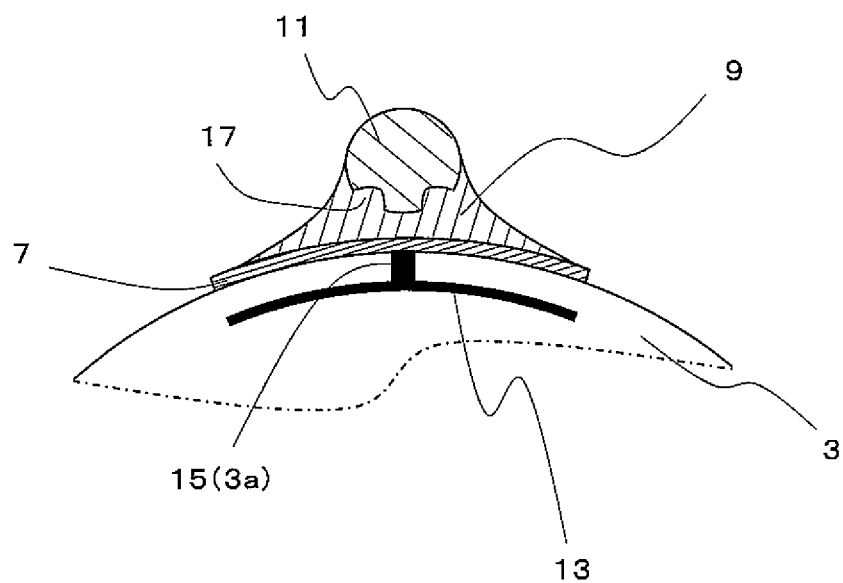
(b)
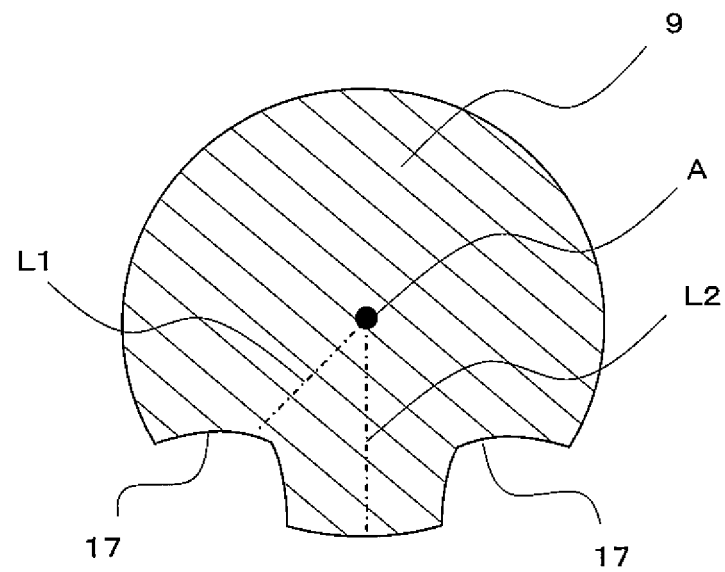

CERAMIC HEATER, OXYGEN SENSOR AND HAIR IRON THAT USE THE CERAMIC HEATER

CROSS-REFERENCE TO THE RELATED APPLICATIONS

This application is a national stage of international application No. PCT/JP2008/069557, filed on Oct. 28, 2008 and claims the benefit of priority under 35 USC 119 to Japanese Patent Application No. 2007-280307, filed on Oct. 29, 2007, the entire contents of which are incorporated herein by reference.

TECHNICAL FIELD

The present invention relates to a ceramic heater that is used in oxygen sensor, air-fuel ratio sensor, glow plug, hair iron and the like.

BACKGROUND ART

Ceramic heaters are used in such applications as heat source for starting an engine, auxiliary heat source for room air heater and heater of air-fuel ratio sensor. An example of ceramic heater used in these applications is a ceramic heater 101 that has such a constitution as shown in FIG. 7, where a heating resistor is embedded in a ceramic base 103, and a lead member 111 is connected via a brazing material 109 to an external electrode 107 (electrode pad) that is electrically connected to the end of the heating resistor (Patent Document 1). FIG. 7 is sectional view showing the ceramic heater of the prior art in a section perpendicular to the longitudinal direction of the lead member.
Patent Document 1: Japanese Unexamined Patent Publication (Kokai) No. 2005-331502

DISCLOSURE OF THE INVENTION

Problems to be Solved by the Invention

The ceramic heater used in the applications described above is subjected to stress such as tension and torsion caused by repetitive thermal cycle and/or vibration during operation. When the ceramic heater receives intense stress repetitively, the interface between the external electrode and the lead member that is bonded together by the brazing material is significantly influenced by the stress, which may deteriorate the bonding between the lead member and the brazing material. It has recently been required for ceramic heaters to have durability high enough to endure such a harsh operating environment as the temperature is raised at a higher rate or higher temperatures are experienced.

The lead member 111 of the conventional ceramic heater 101 has circular shape in the section perpendicular to the longitudinal direction as shown in FIG. 7. When the section perpendicular to the longitudinal direction is circular, length of the circumference of this section of the lead member 111 takes the minimum value for a given cross sectional area. The lead member 111 must be made larger in order to increase the contact area that contributes to the bonding strength between the lead member 111 and the brazing material 109.

The present invention has been devised to solve the problem described above, and has an object to provide a ceramic heater that has high durability by increasing the bonding strength between the lead member and the brazing material.

Means for Solving the Problems

A ceramic heater of the present invention comprises a ceramic base, a heating resistor embedded in the ceramic base, an external electrode that is disposed on side face of the ceramic base and is electrically connected to the heating resistor, and a lead member brazed onto the external electrodes, wherein the distance between a point in the brazed portion of the periphery of the lead member and a center of the lead member is smaller than the distance between an another point in the brazed portion and the center, in a section of the lead member perpendicular to the longitudinal direction of the lead member.

It is preferable that the lead member has a recess in the brazed portion in the section perpendicular to the longitudinal direction. Further it is more preferable that the recess is filled with the brazing material.

It is also preferable that the recess opens on the side of the ceramic base. The lead member preferably has a plurality of the recesses. It is more preferable that the lead member has a plurality of the recesses in one section perpendicular to the longitudinal direction. It is furthermore preferable that the lead member has the recess in each of two regions divided by a straight line that runs through the center of the lead member and the center of the ceramic base in the section perpendicular to the longitudinal direction. It is furthermore preferable that the lead member has recesses located at positions that are symmetrical with respect to the straight line. It is also preferable that the lead member is covered by the brazing material over the entire circumference of the section perpendicular to the longitudinal direction.

An oxygen sensor of the present invention is characterized in that it has one of the ceramic heaters of the present invention described above. A hair iron of the present invention is characterized in that it has one of the ceramic heaters of the present invention described above.

Effects of the Invention

In the ceramic heater of the present invention, the distance between a point in the brazed portion of the periphery of the lead member and the center of the lead member is smaller than the distance between another point in the brazed portion and the center, in a section of the lead member perpendicular to the longitudinal direction. As a result, bonding area between the lead member and the brazing material may be made larger so as to effectively achieve anchoring effect and wedge effect, and therefore it is made possible to increase the bonding strength between the lead member and the brazing material, specifically tensile strength and torsional strength. Thus high durability may be maintained even in such an environment as the temperature is quickly raised and lowered repetitively, or the temperature is repetitively raised and lowered by a great amount.

The oxygen sensor of the present invention has one of the ceramic heaters of the present invention described above, and is therefore capable of maintaining high durability even when the temperature is quickly raised and lowered.

The hair iron of the present invention has one of the ceramic heaters of the present invention described above, and is therefore capable of maintaining high durability even when the temperature is quickly raised and quickly lowered.

BEST MODE FOR CARRYING OUT THE INVENTION

An embodiment of the ceramic heater of the present invention will be described below with reference to the accompanying drawings. FIG. 1 shows an example of the embodiment of the ceramic heater of the present invention, FIG. 1(a) being a perspective view, and FIG. 1(b) being an enlarged perspective view of the external electrode (electrode pad) and the surrounding thereof of the ceramic heater according to the embodiment shown in FIG. 1(a). FIG. 2(a) is an enlarged sectional view in a section perpendicular to the longitudinal direction of the lead member of the ceramic heater according to the embodiment shown in FIG. 1, and FIG. 2(b) is an enlarged sectional view of the lead member shown in FIG. 2(a).

As shown in FIG. 1 and FIG. 2, the ceramic heater 1 of this embodiment comprises a ceramic base 3, a heating resistor 5 embedded in the ceramic base 3, electrode pads 7 that are disposed on the side face of the ceramic base 3 and are electrically connected to the heating resistor 5 and lead members 11 that are brazed onto the electrode pads 7 via a brazing material 9.

The heating resistor 5 is connected to a lead-out pattern 13 embedded in the ceramic base 3. The lead-out pattern 13 is connected to the electrode pad 7 via a through hole conductor 15 that is provided on the inner surface of a through hole 3a which is formed in the ceramic base 3. The heating resistor 5 and the electrode pads 7 are electrically connected to each other in this way.

As shown in FIG. 2, in the ceramic heater 1 of this embodiment, the distance L1 between a point in the brazed portion of the periphery of the lead member 11 and the center A of the lead member 11 is smaller than the distance L2 between another point in the brazed portion and the center A, in a section of the lead member 11 perpendicular to the longitudinal direction of the lead member 11, and the section has a non-circular shape. Therefore, the surface area (or the circumferential length of the section perpendicular to the longitudinal direction) may be made larger for a given sectional area than in the case of the conventional lead member. As a result, bonding area between the lead member 11 and the brazing material 9 may be increased, so as to increase the bonding strength between the lead member 11 and the brazing material 9.

In case the lead member having circular cross section is used, since every point on the circumference of the lead member is at the same distance from the center, it is easy for the lead member to rotate about the center and therefore there is a possibility that the lead member comes off the brazing material. However, in the lead member 11 of the ceramic heater 1 of this embodiment, the distance L1 between a point in the brazed portion of the periphery of the lead member 11 and the center A of the lead member 11 is smaller than the distance L2 between another point in the brazed portion and the center A, and therefore the portion located at the greater distance from the center acts as an anchor that hitches onto the brazed material 9 so that the rotation described above is suppressed by the anchoring effect. As a result, since bonding strength between the lead member 11 and the brazing material 9 may be improved also mechanically, peel-off of the lead member 11 from the brazing material 9 may be effectively suppressed.

FIG. 3(a) to FIG. 3(c) are sectional views showing another example of the embodiment of the ceramic heater according to the present invention, respectively. As shown in FIG. 3, it is preferable that the lead member 11 has a recess 17 in the portion brazed in the section perpendicular to the longitudinal direction. As the lead member 11 has the recess 17, it is made possible to improve bonding between the lead member 11 and the brazing material 9 and suppress complete peel-off of the lead member 11 from the brazing material 9.

This is because bonding interface between the lead member 11 and the brazing material 9 is subjected to stress and, even when peel-off takes place in a part of the bonding interface, the peel-off is suppressed from proceeding in the recess 17 since the surface of the recess 17 has a smaller radius of curvature in the surface of the lead member 11. As a result, complete peel-off of the lead member 11 from the brazing material 9 is suppressed and the heating resistor 5 may be stably energized.

Further as shown in FIG. 3(b), it is more preferable that the recess 17 is filled with the brazing material 9. This is because filling the recess 17 of the lead member 11 with the brazing material 9 makes it possible to increase the bonding area between the lead member 11 and the brazing material 9 further, and achieve higher anchoring effect due to the increasing size of the protrusion of the brazing material 9 that serves as the wedge.

It is also preferable that the recess 17 has a curved surface as shown in FIG. 3. This is because stress may be suppressed from being concentrated when the recess 17 has a curved surface and no sharp portion is formed thereon. It is particularly preferable that the recess 17 has a semi-spherical surface.

Further as shown in FIG. 3(c), it is preferable that the recess 17 opens on the side of the ceramic base 3. This makes it easy to fill the recess 17 with the brazing material 9, so that the recess 17 may be more reliably filled with the brazing material 9. This makes it possible to achieve a higher bonding strength between the lead member 11 and the brazing material 9 and provide the ceramic heater having higher durability.

FIG. 4(a) to FIG. 4(c) are enlarged sectional views showing another example of the embodiment of the ceramic heater according to the present invention, respectively. Another preferable shape of the section perpendicular to the longitudinal direction of the lead member 11 is a polygon represented by the rectangular shape shown in FIG. 4(a). When the cross section of the lead member 11 has a polygonal shape, the lead member 11 has a simple configuration that may be easily formed, and the surface area may be made larger thereby improving the bonding strength. Also because the lead member 11 has corners, mechanical connection may be improved as the corners are retained by the brazing material 9.

Also as shown in FIG. 4(b), it is preferable that the lead member 11 has a protrusion 21 in the portion brazed in the section perpendicular to the longitudinal direction. This is because higher effect of suppressing the rotation may be achieved by increasing the surface area further and providing the protrusion 21, in comparison to the form shown in FIG. 4(a).

Because of high bonding strength between the lead member 11 and the brazing material 9, the ceramic heater of the embodiment shown in FIGS. 4(a), 4(b) is particularly advantageous when used in an environment that requires higher bonding strength between the lead member 11 and the brazing material 9 such as one where significant thermal cycles or vibrations are repetitively applied.

The section perpendicular to the longitudinal direction of the lead member 11 is preferably elliptical as shown in FIG. 4(c). In this case, bonding strength between the lead member 11 and the brazing material 9 may be improved similarly to the case of the embodiment shown in FIG. 2 and FIGS. 4(a), 4(b), as well as to mechanically improve the bonding strength. In case a section perpendicular to the longitudinal direction of the lead member 11 is elliptical as shown in FIG. 4(c), stress may be suppressed from being locally concentrated because the bonding interface between the lead member 11 and the brazing material 9 is curved without corners.

In case the lead member 11 has the recess 17, it is preferable that a plurality of recesses 17 are provided. This is because, when the lead member 11 has a plurality of recesses 17 as shown in FIG. 2, the bonding area between the lead member 11 and the brazing material 9 may be increased further. Providing a plurality of recesses 17 also results in the formation of a plurality of protrusions of the brazing material 9 that serve as wedges, so as to achieve higher anchoring effect. Also because the stress generated in the bonding interface between the lead member 11 and the brazing material 9 may be dispersed in the recesses 17, durability may be improved further.

FIG. 5(a) to FIG. 5(c) are sectional views showing another example of the embodiment of the ceramic heater according to the present invention, respectively. As shown in FIG. 5(a) to FIG. 5(c), it is preferable that the lead member 11 has a plurality of recesses 17 in a section perpendicular to the longitudinal direction. Providing a plurality of recesses 17 in this way makes it possible to disperse the stress, that acts in the direction in which the lead member 11 is twisted, in each of the recesses 17, and therefore durability may be improved further.

Further as shown in FIG. 5(b) and FIG. 5(c), it is more preferable that the lead member 11 has the recess 17 in each of two regions that are divided by a straight line B that runs through the center of the lead member 11 and the center of the ceramic base 3 in a section perpendicular to the longitudinal direction. In an environment where significant thermal cycles or large vibrations are repetitively applied, the lead member 11 is subjected to stress generated therein mainly by the movement of the ceramic base 3 via the brazing material 9. Forming the recess 17 in the lead member 11 enables it to improve the durability against stress acting in the straight line that runs through the center of the lead member 11 and the center of the ceramic base 3 (vertical direction in the case shown in FIG. 5(b) and FIG. 5(c)). In addition, forming the recess 17 in each of the two regions as described above makes it possible to improve the durability against stress generated by thermal cycles in the direction perpendicular to the straight line described above (horizontal direction in the case shown in FIG. 5(b) and FIG. 5(c)), as well durability against stress generated in the direction of the line described above.

Further as shown in FIG. 5(c), it is more preferable that the lead member 11 has the recesses 17 at positions symmetrically located with respect to straight line B. This configuration makes it possible to disperse the stress evenly in each of the recesses 17, also with regard to the stress that acts in the direction perpendicular to the straight line described above, so as to improve the bonding strength between the lead member 11 and the brazing material 9 further.

FIG. 6 is a sectional view showing another example of the embodiment of the ceramic heater according to the present invention. As shown in FIG. 6, it is preferable that the lead member 11 is covered by the brazing material 9 over the entire circumference section perpendicular to the longitudinal direction. When the lead member 11 is covered by the brazing material 9 in this way, it is made possible to suppress peel-off of the lead member 11 from the brazing material 9 in the direction opposite to the ceramic base 3 side (vertical direction in the case shown in FIG. 6).

A method for manufacturing the ceramic heater of the present invention will be described below.

The ceramic base 3 may be formed from ceramics that has insulating property such as oxide ceramics, nitride ceramics or carbide ceramics. Specifically, alumina-based ceramics, silicon nitride-based ceramics, aluminum nitride-based ceramics or silicon carbide-based ceramics may be used. Particularly, from the view point of oxidation resistance, it is preferable to use alumina-based ceramics.

The ceramic base 3 may have, for example, cylindrical shape measuring about 2 to 20 mm in diameter and 40 to 60 mm in length. Particularly, for the ceramic heater used to heat the air-fuel ratio sensor of automobile, it is preferable that the ceramic base 3 measures about 2 to 4 mm in diameter and 40 to 65 mm in length, in order to suppress a portion bonded with the lead member 11 from being heated to an extremely high temperature.

First, in order to fabricate the ceramic base 3, a ceramic slurry prepared by adding 4 to 12% by mass in total of sintering aid such as $SiO_2$, CaO, MgO and $ZrO_2$ to the ceramic component described previously is formed into a sheet, thereby making a ceramic sheet. The ceramic slurry may be constituted from 88 to 95% by mass of $Al_2O_3$, 2 to 7% by mass of $SiO_2$, 0.5 to 3% by mass of CaO, 0.5 to 3% by mass of MgO and 1 to 3% by mass of $ZrO_2$.

The $Al_2O_3$ content is preferably from 88 to 95% by mass, because keeping the content thereof of 88% by mass or more enables it to suppress the concentration of glass component so as to suppress migration from occurring when electric current flows therein. Restricting the content thereof to 95% by mass or less enables it to disperse a sufficient amount of glass component in the heating resistor 5.

An electrically conductive paste that would become the heating resistor 5 and the lead-out pattern 13 are applied by printing or the like onto one principal surface of the ceramic sheet that would become the ceramic base 3. The heating resistor 5 may be formed from a material that includes a metal having a high melting point such as W, Mo or Re. The electrically conductive paste may be prepared by mixing the metal having a high melting point, a ceramic material, a binder, and an organic solvent and the like. The position where heat is generated and the value of electrical resistance may be set as desired by controlling the length of the wrap-around pattern of the electrically conductive paste and the width of line formed by the electrically conductive paste that would become the heating resistor 5.

Then a through hole 3a is formed in the ceramic sheet, and the through hole 3a is filled with an electrically conductive material that includes at least one of W, Mo and Re as main component to form a through hole conductor 15. Further, this is followed by the formation of the electrode pad 7 on one of the principal surfaces of the ceramic sheet by printing or transfer process. The electrode pad 7 may be formed from a metal such as W or Ni.

The ceramic sheet is wound around a ceramic core 23 in close contact therewith by using a bonding liquid, to form a cylindrical green compact. Further, the green compact is fired at a temperature from 1,500 to 1,650° C. in a reducing atmosphere.

It is preferable to form a metal film 25 from a metal such as Ni or Cr on the surface of the electrode pad 7, in order to suppress deterioration due to oxidation. The metal film 25 may be formed by such a method as electroplating, electroless plating, sputtering, thermal spraying or application and drying of a material that includes noble metal particles of submicrometer size. It is preferable that thickness of the metal film 25 is 1 μm or larger so as to suppress the electrode pad 7 from being oxidized. It is also preferable that thickness of the metal film 25 is 5 μm or smaller so as to suppress separation from occurring in the metal film 25.

Then the lead member 11 is bonded onto the electrode pad 7 or the metal film 25 by using the brazing material 9. At this time it is preferable to bond the lead member 11 in a reducing atmosphere that includes water vapor. For the brazing material 9, a material that includes Au—Cu, Ag, Ag—Cu or the like as the main component may be used. The lead member 11 may be formed from a metal having low electrical resistance such as Ni, Ni alloy, platinum, copper or the like.

The ceramic heater 1 of this embodiment uses the lead member 11 wherein the distance between a point in the brazed, portion of the periphery of the lead member 11 and the center of the lead member 11 is smaller than the distance between another point in the brazed portion and the center, in a section perpendicular to the longitudinal direction.

For the lead member 11 that is non-circular in the section perpendicular to the longitudinal direction, for example, one that has a shape of polygonal prism or the lead member 11 of cylindrical shape of which cross section is turned into non-circular shape by applying pressing process or the like to the brazed portion may be used. By using the lead member 11 having such a configuration, it is made possible to increase the bonding area between the lead member 11 and the brazing material 9 and thereby increase the tensile strength and the torsional strength of the bonding portion of the lead member 11.

It is preferable to form a plating layer of Au, Cr, Ni or the like on the surfaces of the electrode pad 7, the brazing material 9 and the lead member 11, because it enables it to suppress the electrode pad 7, the brazing material 9 and the lead member 11 from deteriorating due to oxidization in the operating environment. Thickness of the plating layer is preferably in a range from 1 to 10 μm.

The ceramic heater of this embodiment may be manufactured as described above. The ceramic heater manufactured in this way may be used in a hair iron, an oxygen sensor, soldering iron or the like. The ceramic heater of the present invention is not limited to the embodiment described above, and may be applied to ceramic heaters of various configurations such as cylinder, plate, etc., as long as the configuration allows it to bond the lead member 11 with the brazing material 9.

The hair iron of the present invention will be described below. The hair iron of this embodiment has such a constitution as the ceramic heater exemplified by the embodiment described above is secured onto the tip of a soldering iron made of metal and is connected by the lead member 11 to electric circuits such as temperature regulator. Since the hair iron of this embodiment has the ceramic heater exemplified by the embodiment described above, high durability may be maintained even when the hair iron is operated to heat quickly and cool down quickly.

EXAMPLES

The ceramic heater of the present invention was fabricated as described below.

First, a ceramic green sheet was formed from $Al_2O_3$ as the main component with 10% by mass of $SiO_2$, CaO, MgO and $ZrO_2$ in total added thereto. Then the through hole 3a was formed in the ceramic green sheet, and the through hole 3a was filled with a paste consisting mainly of W to form the through hole conductor 15. The electrically conductive paste that included W—Re as the main component and would become the heating resistor 5 was printed onto the ceramic green sheet by screen printing process. The electrically conductive paste was printed so as to form the heating resistor 5 having length of 5 mm and resistance of 12 to 13Ω after being fired.

Then the electrode pad 7 was formed on the through hole 3a using a paste including W as the main component by screen printing process. This sheet was coated with a bonding liquid that included ceramics of substantially the same composition as that of the ceramic green sheet, and was wound around a ceramic core 23 in close contact therewith and fired at a temperature from 1,500 to 1,600° C. in a reducing atmosphere.

The Ni plating film 25 having thickness of 2 to 4 μm was formed on the electrode pad 7 by electroplating, and the electrode pad 7 and the lead member 11 were bonded together by using the brazing material 9 made of Ag—Cu. The lead member 11 had cylindrical shape measuring 0.8 mm in diameter and 20 mm in length. The lead member 11 of the ceramic heater 1 of each specimen number was process by pressing in advance, so as to form the cross sectional shape of the lead member shown in Table 1. Each specimen of the ceramic heater 1 had dimensions of 3 mm in diameter and 55 mm in length. The electrode pad 7 measured 5 mm by 4 mm, and diameter of the through hole was 500 μm.

The ceramic heater 1 fabricated as described above was subjected to durability test of thermal cycles.

First, the specimen was subjected to 4,000 thermal cycles in a thermostat that was kept at a temperature one half (about 400° C. in the case of a Ag—Cu brazing material) of the melting point of the brazing material 9, each cycle consisting of heating to the temperature described above for 10 minutes and a period of forced cooling with air of 25Ω. After the thermal cycles, a tensile strength test was conducted in which tensile strength of the lead member 11 was measured, and a torsional strength test was conducted in which the torsional strength of the lead member 11 was measured. The tensile strength was measured by securing the ceramic heater and pulling the lead member 11 in the vertically direction at a speed of 32 mm/min while measuring the load at the time of rupture with a load cell. The torsional strength was measured by securing the lead member 11 to a motor, pulling the lead member 11 with a force of 5 N, and running the motor at a speed of 2 turns per minute until crack or peel-off from the brazing material 9 took place in part of the lead member 11. Test results are shown in Table 1.

TABLE 1

| Specimen No. | Cross section of lead member | Number of recesses | Filling recess with brazing material | Position of recess | Presence of recess in each region | Symmetry of plurality of recesses | Covering of brazing material | Tensile strength of the lead member after thermal cycle test (N) | State after tensile strength test of lead member after thermal cycle test | |
|---|---|---|---|---|---|---|---|---|---|---|
| 1 | FIG. 7 | 0 | — | — | Not present | Not symmetric | No | 12 | Lead and brazing material peeled off after 1 turns | Energization impossible |
| 2 | FIG. 4(c) | 0 | — | — | Not | Not | No | 22 | Lead and brazing | Energization |

TABLE 1-continued

| Specimen No. | Cross section of lead member | Number of recesses | Filling recess with brazing material | Position of recess | Presence of recess in each region | Symmetry of plurality of recesses | Covering of brazing material | Tensile strength of the lead member after thermal cycle test (N) | State after tensile strength test of lead member after thermal cycle test | |
|---|---|---|---|---|---|---|---|---|---|---|
| | | | | | present | symmetric | | | material peeled off after 2 turns | impossible |
| 3 | FIG. 3(a) | 1 | No | Side | Not present | Not symmetric | No | 35 | Lead and brazing material partially peeled off after 2 turns | Energization possible |
| 4 | FIG. 3(b) | 1 | Yes | Side | Not present | Not symmetric | No | 44 | Lead and brazing material partially peeled off after 2 turns | Energization possible |
| 5 | FIG. 3(c) | 1 | Yes | On substrate | Not present | Not symmetric | No | 72 | Lead and brazing material partially peeled off after 3 turns | Energization possible |
| 6 | FIG. 5(a) | 2 | Yes | On substrate | Not present | Not symmetric | No | 83 | Lead and brazing material partially peeled off after 4 turns | Energization possible |
| 7 | FIG. 5(b) | 2 | Yes | On substrate | Present | Not symmetric | No | 88 | Lead and brazing material partially peeled off after 4 turns | Energization possible |
| 8 | FIG. 5(c) | 2 | Yes | On substrate | Present | Symmetric | No | 93 | Lead and brazing material partially peeled off after 5 turns | Energization possible |
| 9 | FIG. 6 | 2 | Yes | On substrate | Present | Symmetric | Yes | 106 | Lead member partially cracked after 8 turns | Energization possible |

As shown in Table 1, the ceramic heater 1 of specimen No. 1 showed weak tensile strength of 12 N, and particularly low durability in the bonding interface between the lead member 11 and the brazing material 9j. This is because the lead member 11 had cylindrical configuration with the section perpendicular to the longitudinal direction having circular shape, and therefore bonding area between the lead member 11 and the brazing material 9j was small and sufficient anchoring effect was not achieved. As a result, the difference in thermal expansion between the lead member 11 and the brazing material 9 during the thermal cycles caused a gap to be generated between the lead member 11 and the brazing material 9, thus allowing the brazing material 9 to be oxidized through the gap leading to deterioration of the bonding.

In the ceramic heaters 1 of specimens Nos. 2 to 9 in which the lead member 11 had non-circular section perpendicular to the longitudinal direction wherein the distance between a point in the brazed portion of the periphery of the lead member 11 and the center of the lead member 11 is smaller than the distance between another point in the brazed portion and the center, formed by modifying the shape of the lead member 11, in contrast, tensile strength of 22 N or higher was observed indicating that durability was improved in any of these specimens.

With the ceramic heater 1 of specimen No. 2 that had elliptical cross section, tensile strength of 22 N was observed indicating that durability of bonding portion of the lead was improved. It was also confirmed that durability was improved against the stress in the direction of torsion so as to endure up to two turns.

With the ceramic heater 1 of specimen No. 3 that had the recess 17 formed in the side face of the lead member 11 while the recess 17 was not filled with the brazing material 9, the tensile strength was 35 N indicating that durability of the bonding portion of the lead was improved further. It was also confirmed that durability against stress in the direction of torsion was improved so as to endure up to two turns. Also because the recess 17 was formed, peel-off was suppressed from growing into the recess, thus enabling it to keep the peel-off within a local area. As a result, points of local bonding between the lead member 11 and the brazing material 9 remained thereby enabling it to continue to energize the ceramic heater 1. The recess 17 of the ceramic heater 1 of specimen No. 3 was not filled with the brazing material 9, while glass beads were put into the recess 17 as a filling material 19.

With the ceramic heater 1 of specimen No. 4 that had the recess 17 formed in the side face of the lead member 11 while the recess 17 was filled with the brazing material 9, tensile strength was 44 N indicating that durability of the bonding portion of the lead was improved further, because the bonding strength between the lead member 11 and the brazing material 9 was improved by filling the recess 17 with the brazing material 9. It was also confirmed that durability against stress in the direction of torsion was improved so as to endure up to two turns.

With the ceramic heater 1 of specimen No. 5 that had the recess 17 which opened on the side of the ceramic base 3, since it was easy for the recess 17 to be filled with the brazing material 9, tensile strength was 72 N indicating that durability of the bonding portion of the lead was greatly improved. It was also confirmed that durability against stress in the direction of torsion was improved so as to endure up to three turns.

With the ceramic heater 1 of specimen No. 6 that had a plurality of recesses 17 in a section perpendicular to the longitudinal direction, since stress could be dispersed in each of the recesses 17, tensile strength was 83 N indicating that durability of the bonding portion of the lead was improved further. It was also confirmed that durability against stress in the direction of torsion was improved further so as to endure up to four turns. Thus it is proved that providing the plurality of recesses 17 improves the durability against stress that acts in the direction in which the lead member 11 is twisted.

With the ceramic heater 1 of specimen No. 7, since the lead member 11 having the configuration shown in FIG. 5(b) was provided, tensile strength was 88 N indicating that durability of the bonding portion of the lead was improved further. It was also confirmed that durability against stress in the direction of torsion was improved so as to endure up to four turns.

With the ceramic heater 1 of specimen No. 8, since the lead member 11 having the configuration shown in FIG. 5(c) was provided, tensile strength was 93 N indicating that durability of the bonding portion of the lead was improved further. It was also confirmed that durability against stress in the direction of torsion was improved further so as to endure up to five turns.

With the ceramic heater 1 of specimen No. 9, since the lead member 11 having the configuration shown in FIG. 6 was provided, tensile strength was 106 N indicating that durability of the bonding portion of the lead was improved further. With regard to durability against stress in the direction of torsion, crack occurred in part of the lead member 11 after making eight turns. However, peel-off did not occur in bonding interface between the lead member 11 and the brazing material 9, thus proving very high bonding performance.

BRIEF DESCRIPTION OF THE DRAWINGS

FIG. 1 shows an example of the embodiment of the ceramic heater of the present invention, FIG. 1(a) in a perspective view, and FIG. 1(b) in an enlarged perspective view of the embodiment shown in FIG. 1(a).

FIG. 2(a) is an enlarged sectional view in a section perpendicular to the longitudinal direction of the lead member of the ceramic heater according to the embodiment shown in FIG. 1, and FIG. 2(b) is an enlarged sectional view of the lead member of the embodiment shown in FIG. 2(a).

Figure 3:
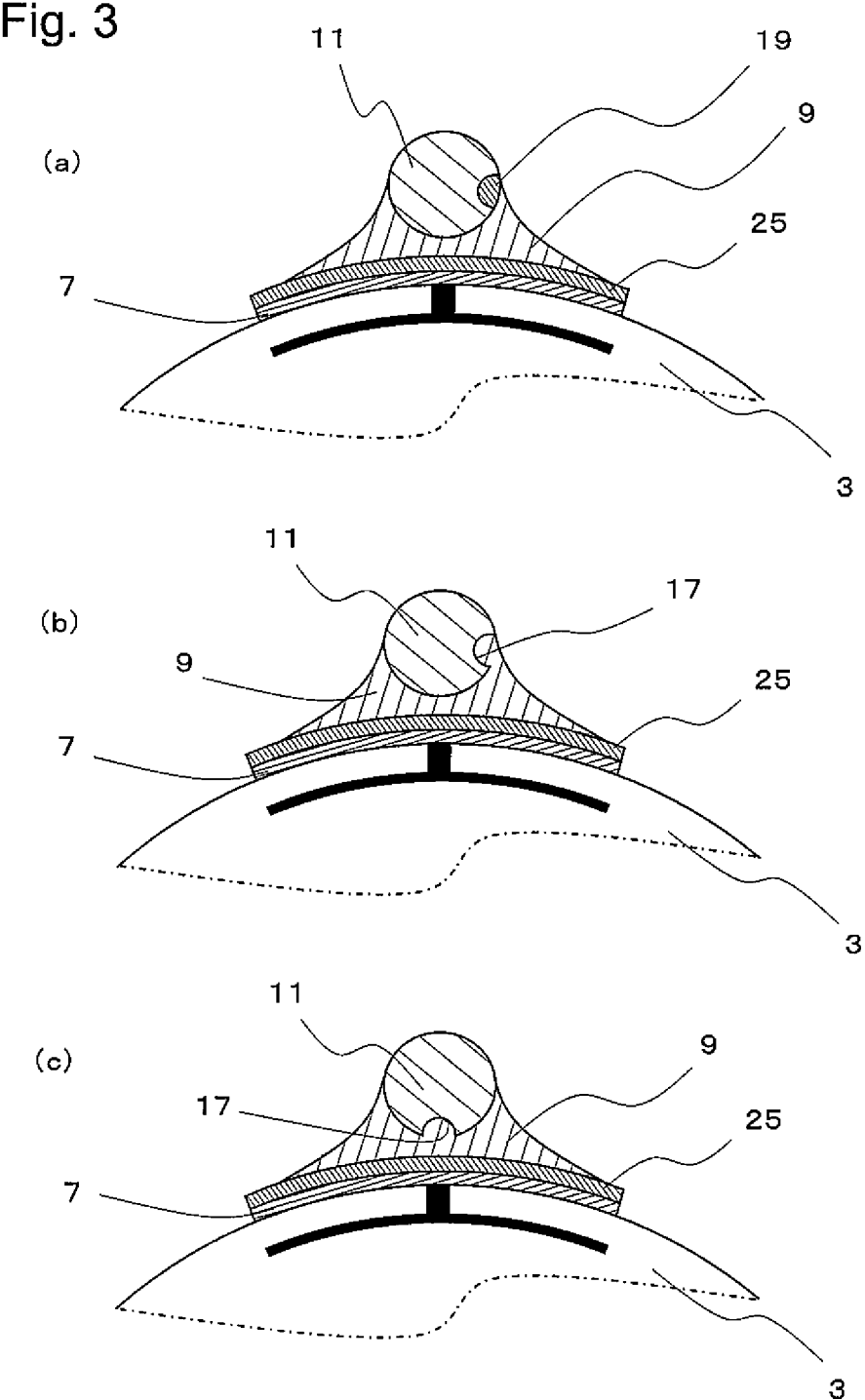
FIG. 3(a) to FIG. 3(c) are sectional views showing another example of the embodiment of the ceramic heater according to the present invention.
Figure 4:
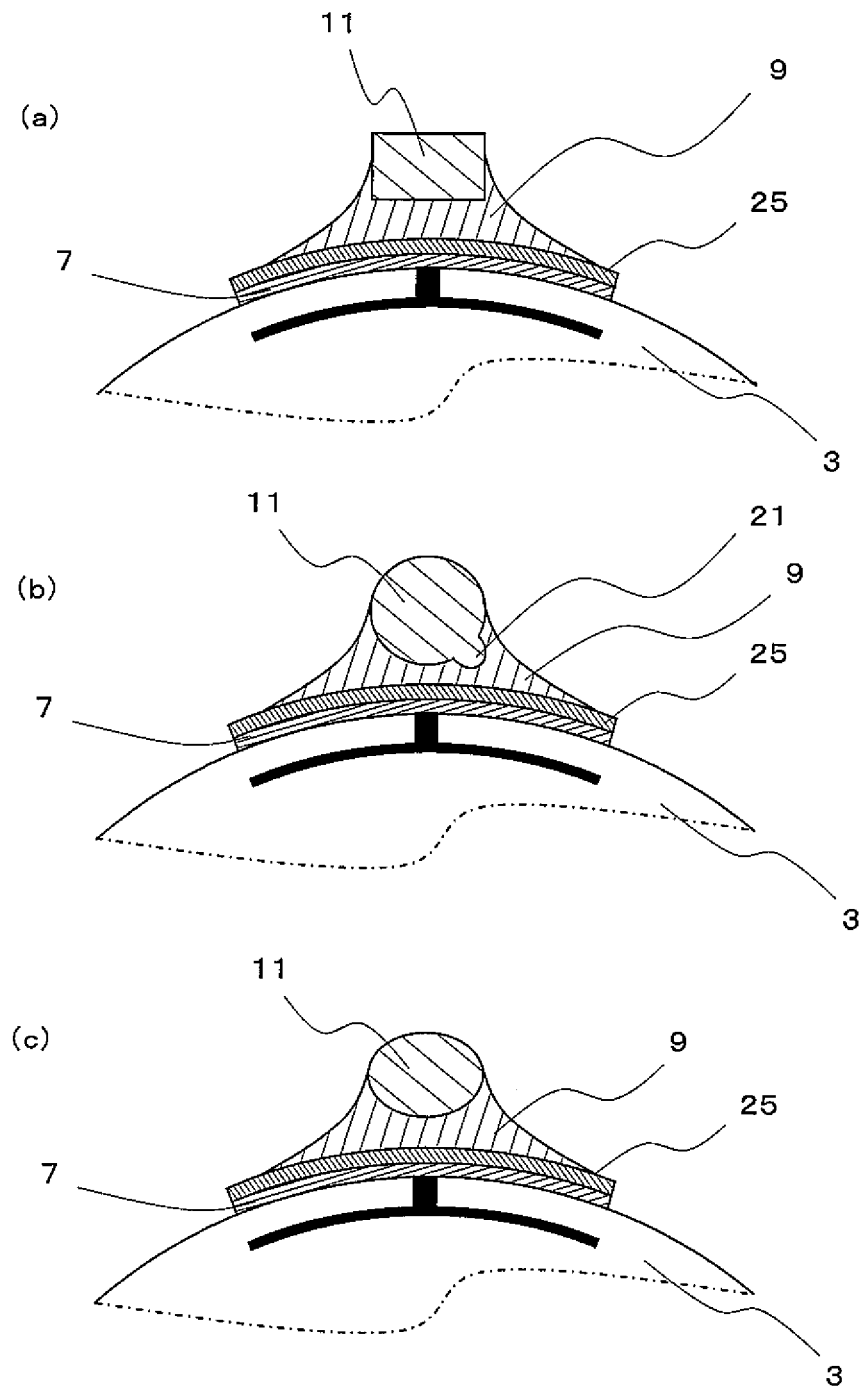
FIG. 4(a) to FIG. 4(c) are sectional views showing another example of the embodiment of the ceramic heater according to the present invention.
Figure 5:
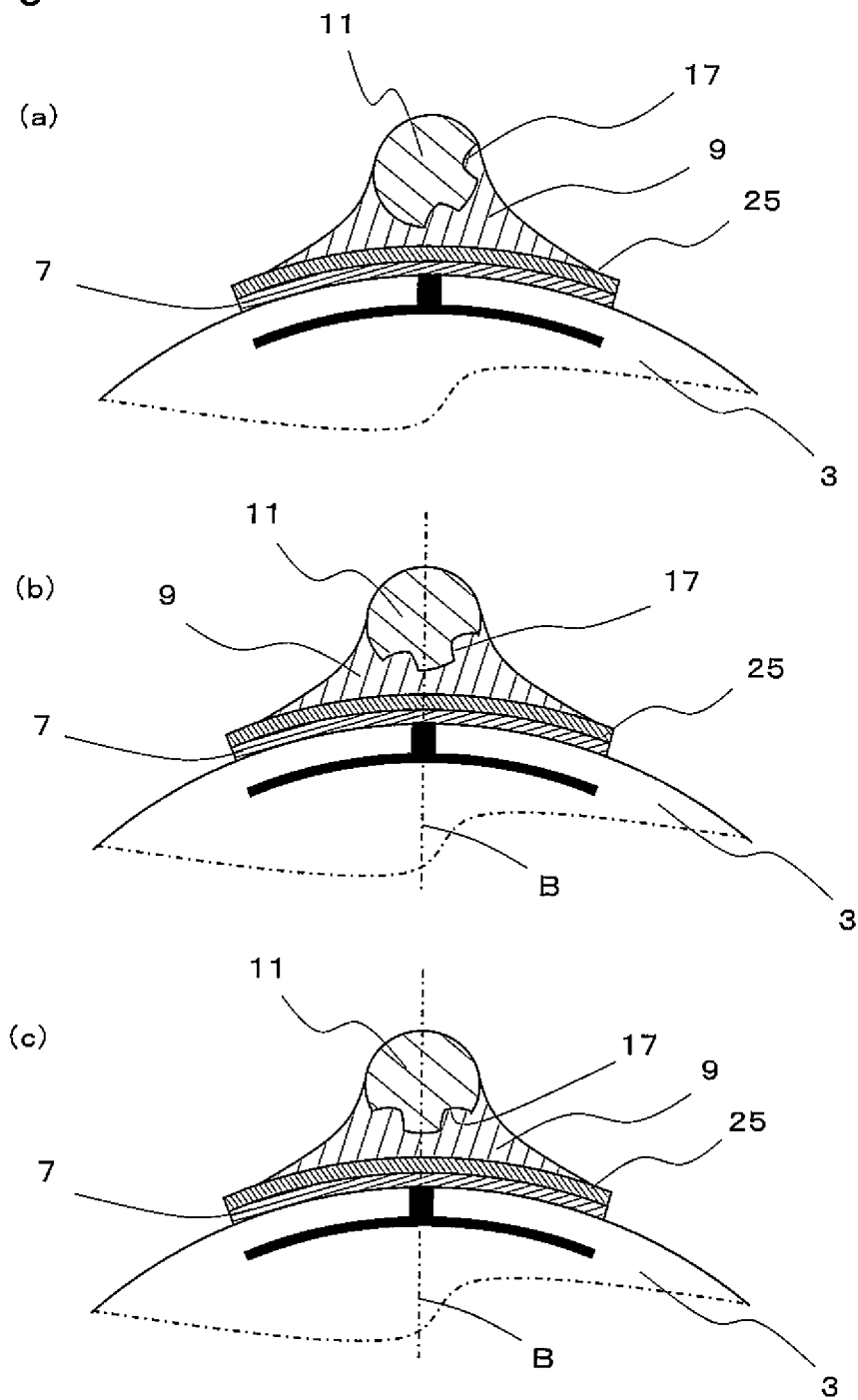
FIG. 5(a) to FIG. 5(c) are sectional views showing another example of the embodiment of the ceramic heater according to the present invention.
Figure 6:
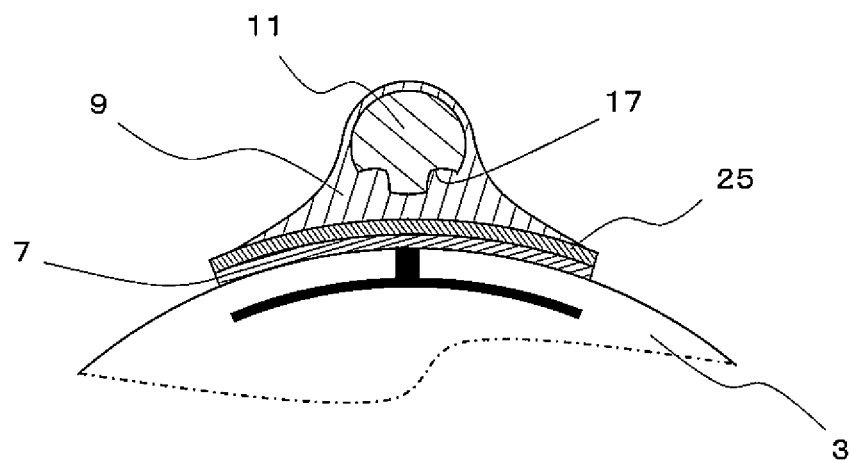
FIG. 6 is a sectional view showing another example of the embodiment of the ceramic heater according to the present invention.
Figure 7:
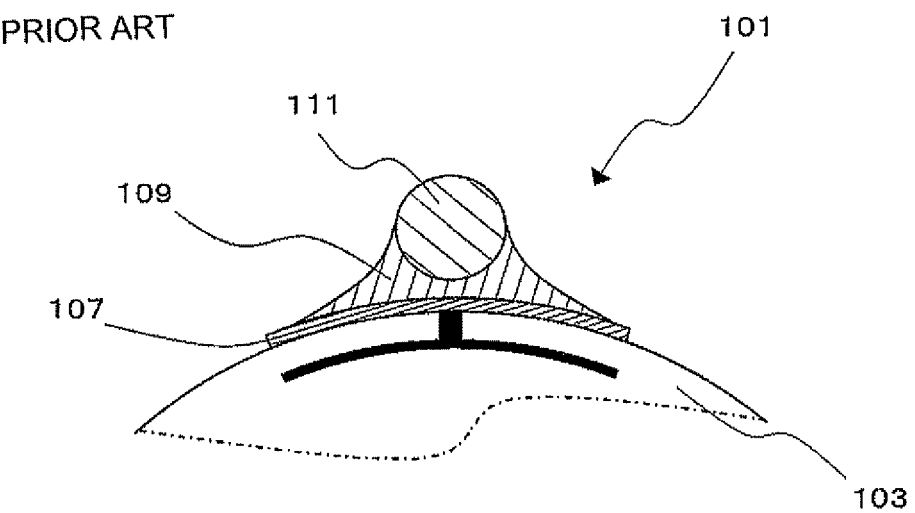
FIG. 7 shows the ceramic heater of the prior art in a sectional view of a section perpendicular to the longitudinal direction.

| Description of Reference Numerals | |
|---|---|
| 1, 101 | Ceramic heater |
| 3 | Ceramic substrate |
| 3a | Through hole |
| 5 | Heating resistor |
| 7 | Electrode pad (external electrode) |
| 9, 109 | Brazing material |
| 11, 111 | Lead member |
| 13 | Lead-out pattern |
| 15 | Through hole conductor |
| 17 | Recess |
| 19 | Filling material |
| 21 | Protrusion |
| 23 | Ceramic core |
| 26 | Metal film |

The invention claimed is:

1. A ceramic heater comprising:
a ceramic base;
a heating resistor embedded in the ceramic base;
an external electrode on side face of the ceramic base electrically connected to the heating resistor; and
a lead brazed onto the external electrode,
wherein, in a cross-section of the lead perpendicular to a longitudinal direction thereof, a distance between a first point in a brazed portion of a periphery of the lead and a center of the lead is smaller than a distance between a second point in the brazed portion and the center, and
wherein the lead comprises at least two recesses in the brazed portion in the cross-section, the second point being positioned between the two recesses and facing the ceramic base,
wherein the recesses have a curved surface.

2. The ceramic heater according to claim 1, wherein the recesses are filled with the brazing material.

3. The ceramic heater according to claim 1, wherein the recesses open toward the ceramic base.

4. The ceramic heater as in one of according to claim 1, wherein the lead is covered by the brazing material over the entire circumference in the section perpendicular to the longitudinal direction.

5. An oxygen sensor comprising the ceramic heater according to claim 1.

6. A hair iron comprising the ceramic heater according to claim 1.

* * * * *